(12) United States Patent
Fischer et al.

(10) Patent No.: US 8,420,608 B2
(45) Date of Patent: Apr. 16, 2013

(54) ACTIVE SUBSTANCE COMBINATIONS WITH INSECTICIDES AND ACARICIDE PROPERTIES

(75) Inventors: Reiner Fischer, Monheim (DE); Wolfram Andersch, Bergisch Gladbach (DE); Heike Hungenberg, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 485 days.

(21) Appl. No.: 12/591,267

(22) Filed: Nov. 13, 2009

(65) Prior Publication Data

US 2010/0137233 A1 Jun. 3, 2010

(30) Foreign Application Priority Data

Nov. 14, 2008 (EP) .................................... 08169150

(51) Int. Cl.
 *A01N 43/08* (2006.01)
 *A01N 43/38* (2006.01)
 *A01N 43/22* (2006.01)
 *A01P 7/02* (2006.01)
 *A01P 7/04* (2006.01)

(52) U.S. Cl.
 USPC .............................. 514/28; 514/409; 514/462

(58) Field of Classification Search .................... 514/28, 514/409, 462
 See application file for complete search history.

(56) References Cited

U.S. PATENT DOCUMENTS

| | | | |
|---|---|---|---|
| 5,258,527 A | 11/1993 | Krauskopf et al. |
| 5,262,383 A | 11/1993 | Fischer et al. |
| 5,462,913 A | 10/1995 | Fischer et al. |
| 5,504,057 A | 4/1996 | Fischer et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,683,965 A | 11/1997 | Bachmann et al. |
| 5,830,825 A | 11/1998 | Fischer et al. |
| 5,830,826 A | 11/1998 | Fischer et al. |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,589,976 B1 | 7/2003 | Fischer et al. |
| 6,608,211 B1 | 8/2003 | Hagemann et al. |
| 6,861,391 B1 | 3/2005 | Fischer et al. |
| 6,894,005 B1 | 5/2005 | Maetzke et al. |
| 2003/0216260 A1 | 11/2003 | Ruther et al. |
| 2005/0054535 A1 | 3/2005 | Fischer et al. |
| 2005/0090399 A1 | 4/2005 | Friedmann et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0167188 A1 | 7/2008 | Fischer et al. |
| 2008/0220973 A1 | 9/2008 | Fischer et al. |
| 2008/0305955 A1 | 12/2008 | Bretschneider et al. |
| 2008/0318776 A1 | 12/2008 | Fischer et al. |
| 2009/0012152 A1 | 1/2009 | Fischer et al. |
| 2009/0029858 A1 | 1/2009 | Fischer et al. |
| 2009/0215624 A1 | 8/2009 | Fischer et al. |
| 2009/0239906 A1 | 9/2009 | Fischer et al. |
| 2009/0281157 A1 | 11/2009 | Fischer et al. |
| 2009/0298828 A1 | 12/2009 | Fischer et al. |
| 2010/0009850 A1 | 1/2010 | Fischer et al. |
| 2010/0168226 A1 | 7/2010 | Fischer et al. |
| 2010/0279873 A1 | 11/2010 | Fischer et al. |
| 2011/0086762 A1 | 4/2011 | Fischer et al. |

FOREIGN PATENT DOCUMENTS

| | | |
|---|---|---|
| CA | 2 633 525 A1 | 7/2007 |
| CA | 2 642 787 A1 | 8/2007 |
| CA | 2 671 179 A1 | 6/2008 |
| CA | 2 695 032 A1 | 2/2009 |
| DE | 10 2005059892 A1 | 6/2007 |
| EP | 0 456 063 A2 | 11/1991 |
| EP | 0 521 334 A1 | 1/1993 |
| EP | 0 528 156 A1 | 2/1993 |
| EP | 0 596 298 A2 | 5/1994 |
| EP | 0 613 884 A2 | 9/1994 |
| EP | 0 613 885 A2 | 9/1994 |
| EP | 0 647 637 A1 | 4/1995 |
| EP | 0 668 267 A1 | 8/1995 |
| JP | 2002/205984 A2 | 7/2002 |
| WO | WO 89/10396 A1 | 11/1989 |
| WO | WO 95/01971 A1 | 1/1995 |
| WO | WO 95/20572 A1 | 8/1995 |
| WO | WO 95/26954 A1 | 10/1995 |
| WO | WO 96/20196 A1 | 7/1996 |

(Continued)

OTHER PUBLICATIONS

Fischer, R. et al., "Spirotetramat (Movento)—discovery, synthesis and physicochemical properties," Bayer CropScience Journal, vol. 61 (2), pp. 127-140 (2008).*

(Continued)

*Primary Examiner* — John Pak
(74) *Attorney, Agent, or Firm* — Sterne, Kessler, Goldstein & Fox P.L.LC.

(57) ABSTRACT

The novel active compound combinations comprising compounds of the formula (I) and spinetoram have very good insecticidal and/or acaricidal properties.

14 Claims, No Drawings

FOREIGN PATENT DOCUMENTS

| | | |
|---|---|---|
| WO | WO 96/25395 A1 | 8/1996 |
| WO | WO 96/33270 A1 | 10/1996 |
| WO | WO 96/35664 A1 | 11/1996 |
| WO | WO 97/00265 A1 | 1/1997 |
| WO | WO 97/01535 A1 | 1/1997 |
| WO | WO 97/02243 A1 | 1/1997 |
| WO | WO 97/36868 A1 | 10/1997 |
| WO | WO 97/43275 A2 | 11/1997 |
| WO | WO 98/05638 A2 | 2/1998 |
| WO | WO 98/06721 A1 | 2/1998 |
| WO | WO 98/25928 A1 | 6/1998 |
| WO | WO 99/16748 A1 | 4/1999 |
| WO | WO 99/24437 A1 | 5/1999 |
| WO | WO 99/43649 A1 | 9/1999 |
| WO | WO 99/48869 A1 | 9/1999 |
| WO | WO 99/55673 A1 | 11/1999 |
| WO | WO 01/23354 A2 | 4/2001 |
| WO | WO 01/17972 A2 | 9/2001 |
| WO | WO 01/74770 A1 | 10/2001 |
| WO | WO 02/077005 A1 | 10/2002 |
| WO | WO 03/013249 A1 | 2/2003 |
| WO | WO 03/062244 A1 | 7/2003 |
| WO | WO 2004/007448 A1 | 1/2004 |
| WO | WO 2004/024688 A1 | 3/2004 |
| WO | WO 2004/065366 A1 | 8/2004 |
| WO | WO 2004/080962 A1 | 9/2004 |
| WO | WO 2004/111042 A1 | 12/2004 |
| WO | WO 2005/044791 A2 | 5/2005 |
| WO | WO 2005/044796 A1 | 5/2005 |
| WO | WO 2005/048710 A1 | 6/2005 |
| WO | WO 2005/049569 A1 | 6/2005 |
| WO | WO 2005/066125 A1 | 7/2005 |
| WO | WO 2005/092897 A2 | 10/2005 |
| WO | WO 2006/000355 A1 | 1/2006 |
| WO | WO 2006/024411 A2 | 3/2006 |
| WO | WO 2006/029799 A1 | 3/2006 |
| WO | WO 2006/056281 A1 | 6/2006 |
| WO | WO 2006/056282 A1 | 6/2006 |
| WO | WO 2006/077071 A2 | 7/2006 |
| WO | WO 2006/089633 A2 | 8/2006 |
| WO | WO 2007/024782 A2 | 3/2007 |
| WO | WO 2007/048545 A2 | 5/2007 |
| WO | WO 2007/073856 A2 | 7/2007 |
| WO | WO 2007/096058 A1 | 8/2007 |
| WO | WO 2007/121868 A1 | 11/2007 |
| WO | WO 2007/140881 A1 | 12/2007 |
| WO | WO 2008/067873 A1 | 6/2008 |
| WO | WO 2008/067910 A1 | 6/2008 |
| WO | WO 2008/067911 A1 | 6/2008 |
| WO | WO 2008/083950 A2 | 7/2008 |
| WO | WO 2008/138551 A2 | 11/2008 |
| WO | WO 2009/015801 A1 | 2/2009 |
| WO | WO 2009/039975 A1 | 4/2009 |
| WO | WO 2009/049851 A1 | 4/2009 |
| WO | WO 2009/115262 A1 | 9/2009 |
| WO | WO 2010/023171 A2 | 3/2010 |

OTHER PUBLICATIONS

Spinetoram Product Safety Assessment, Dow Chemical Company, Apr. 29, 2008.*
Chloridis, A., et al., "Spinetoram (XDE 175): a New Spinosyn," *Proc. XVI Int. Plant Protection Congress*, 1:68-73, BCPC, United Kingdom (2007).
Colby, S., et al., "Calculating Synergistic and Antagonistic Responses of Herbicide Combinations," *Weeds*, 15:20-22, Weed Science Society of America, United States (1967).
Ito, M., et al., "Synthesis and Insecticidal Activity of Novel N-Oxydihydropyrrole Derivatives with a Substituted Spirocyclohexyl Group," *Biosci. Biotech. Biochem.*, 67:1230-1238, Japan Society for Bioscience, Biotechnology and Agrochemistry, Japan (2003).
English language Abstract of German Patent Publication No. DE 102005059892.
English language Abstract of Japanese Patent Publication No. JP 2002205984.

Search Report for Application No. EP 08 169 150, European Patent Office, Munich, mailed on May 4, 2009.
Bauer, T.A., et al., "Response of Selected Weed Species to Postemergence Imazethapyr and Bentazon," *Weed Tech.* 9:236-242, The Weed Science Society of America (1995).
Blackshaw, R.E., "HOE-39866 Use in Chemical Fallow Systems," *Weed Tech.* 3:420-428, The Weed Science Society of America (1989).
Blackshaw, R.E., "Synergistic Mixes of DPX-A7881 and Clopyralid in Canola (*Brassica napus*)," *Weed Tech.* 3:690-695, The Weed Science Society of America (1989).
Blackshaw, R.E., et al., "Herbicide Combinations for Postemergent Weed Control in Safflower (*Carthamus tinctorius*)," *Weed Tech.* 4:97-104, The Weed Science Society of America (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America (2000).
Buker, III, R.S., et al., "Confirmation and Control of a Paraquat-Tolerant Goosegrass (*Eleusine indica*) Biotype," *Weed Tech.* 16:309-313, The Weed Science Society of America (2002).
Burke, I.C., et al., "CGA-362622 Antagonizes Annual Grass Control with Clethodim," *Weed Tech.* 16:749-754, The Weed Science Society of America (2002).
Flint, J.L., et al., "Analyzing Herbicide Interactions, A Statistical Treatment of Colby's Method." *Weed Tech.* 2:304-309, The Weed Science Society of America (1988).
Gillespie, G.R., and Nalewaja, J.D., "Wheat (*Triticum aestivum*) Response to Triallate Plus Chlorsulfuron," *Weed Tech.* 3:20-23, The Weed Science Society of America (1989).
Green, J.M., et al., "Metribuzin and Chlorimuron Mixtures for Preemergence Broadleaf Weed Control in Soybeans, Glycine max," *Weed Tech.* 2:355-363, The Weed Science Society of America (1988).
Harker, K.N., and O'Sullivan, P.A., "Synergistic Mixtures of Sethoxydim and Fluazifop on Annual Grass Weeds," *Weed Tech.* 5:310-316, The Weed Science Society of America (1991).
Kent, L.M., et al., "Effect of Ammonium Sulfate, Imazapyr, and Environment on the Phytotoxicity of Imazethapyr," *Weed Tech.* 5:202-205, The Weed Science Society of America (1991).
Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America (1996).
Lanclos, D.Y., et al., "Glufosinate Tank-Mix Combinations in Glufosinate-Resistant Rice (*Oryza sative*)," *Weed Tech.* 16:659-663, The Weed Science Society of America (2002).
Norris, J.L., et al., "Weed Control from Herbicide Combinations with Three Formulations of Glyphosate," *Weed Tech.* 15:522-558, The Weed Science Society of America (2001).
Novosel, K.M., et al., "Metolachlor Efficacy as Influenced by Three Acetolactate Synthase-Inhibiting Herbicides, " *Weed Tech.* 12:248-253, The Weed Science Society of America (1998).
Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).
Rummens, F.H.A., "An Improved Definition of Synergistic and Antagonistic Effects," *Weed Science* 23(1):4-6, The Weed Science Society of America, United States (1975).
Salzman, F.P., and Renner, K.A., "Response of Soybean to Combinations of Clomazone, Metribuzin, Linuron, Alachlor, and Atrazine," *Weed Tech.* 6:922-929, The Weed Science Society of America (1992).
Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America (1998).
Shaw, D.R. and Arnold, J.C., "Weed Control from Herbicide Combinations with Glyphosate," *Weed Tech.* 16:1-6, The Weed Science Society of America (2002).
Snipes, C.E., and Allen, R.L., "Interaction of Graminicides Applied in Combination with Pyrithiobac," *Weed Tech.* 10:889-892, The Weed Science Society of America (1996).

Sun, Y.-P. & Johnson, E.R., "Analysis of Joint Action of Insecticides Against House Flies", *J. Econ. Entomol.* 53:887-892, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea spp.*) Species," *Weed Tech.* 11:152-156, The Weed Science Society of America (1997).

Zhang, W., et al., "Fenoxaprop Interactions for Barnyardgrass (*Echinochloa crusgalli*) Control in Rice," *Weed Tech.* 19:293-297, The Weed Science Society of America (2005).

* cited by examiner

ACTIVE SUBSTANCE COMBINATIONS WITH INSECTICIDES AND ACARICIDE PROPERTIES

The present invention relates to novel active compound combinations consisting of, firstly, known cyclic ketoenols and, secondly, other known insecticidally active compounds, which combinations are highly suitable for controlling animal pests such as insects and/or unwanted acarids.

It is already known that certain cyclic ketoenols have herbicidal and/or insecticidal and/or acaricidal properties. At low application rates, the activity of these compounds, though good, is unsatisfactory in certain cases.

Known compounds having a herbicidal and/or insecticidal and/or acaricidal action are 1H-3-arylpyrrolidine-2,4-dione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 06/077071, WO 07/048,545, WO 07/073, 856, DE-A-2005/059892, WO 07/096,058, WO 07/121,868, WO 07/140,881, WO 08/067,873, WO 08/067,910, WO 08/067,911, WO 08/138,551, WO 09/015,801, WO 09/039, 975, WO 09/049,851, PCT/EP2009/001897, EP-08170489). Moreover, ketal-substituted 1H-arylpyrrolidine-2,4-diones are known from WO 99/16748 and (spiro)ketal-substituted N-alkoxyalkoxy-substituted arylpyrrolidinediones are known from JP-A-14 205 984 and Ito M. et al. Bioscience, Biotechnology and Biochemistry 67, 1230-1238, (2003). The addition of safeners to ketoenols is likewise known in principle from WO 03/013249. Moreover, WO 06/024411 discloses herbicidal compositions comprising ketoenols.

It is known that certain $\Delta^3$-dihydrofuran-2-one derivatives have herbicidal, insecticidal or acaricidal properties: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 06/089633, WO 07/048,545 and WO 07/073,856, WO 08/067,911, WO 08/083,950, WO 09/015,801, WO 09/039, 975.

It has now been found that active compound combinations comprising compounds of the formula (I)

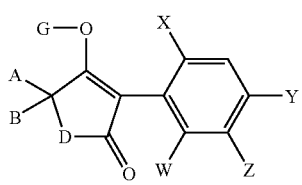

in which
X represents halogen, alkyl, alkoxy, haloalkyl, haloalkoxy or cyano,
W, Y and Z independently of one another represent hydrogen, halogen, alkyl, alkoxy, haloalkyl, haloalkoxy or cyano,
A represents hydrogen, in each case optionally halogen-substituted alkyl, alkoxyalkyl, or saturated, optionally substituted cycloalkyl in which optionally at least one ring atom has been replaced by a heteroatom,
B represents hydrogen or alkyl,
or
A and B together with the carbon atom to which they are attached represent a saturated or unsaturated, unsubstituted or substituted cycle which optionally contains at least one heteroatom,
D represents NH or oxygen,
G represents hydrogen (a) or represents one of the groups

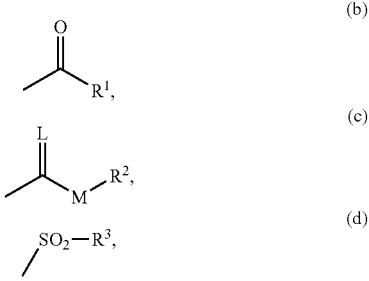

in which
E represents a metal ion or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$ represents optionally halogen-substituted alkyl or optionally substituted phenyl,
$R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and
$R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the nitrogen atom to which they are attached represent an optionally substituted ring which is optionally interrupted by oxygen or sulphur in the form of their isomer mixtures or pure isomers
and
spinetoram
known from WO 97/00265
have very good insecticidal and/or acaricidal properties.

Preference is given to using active compound combinations comprising compounds of the formula (I) mentioned above in which the radicals have the following meaning:

W preferably represents hydrogen, $C_1$-$C_4$-alkyl, $C_1$-$C_4$-alkoxy, chlorine, bromine or fluorine, X preferably represents $C_1$-$C_4$-alkyl, $C_1$-$C_4$-alkoxy, $C_1$-$C_4$-haloalkyl, fluorine, chlorine or bromine, Y and Z independently of one another preferably represent hydrogen, $C_1$-$C_4$-alkyl, halogen, $C_1$-$C_4$-alkoxy or $C_1$-$C_4$-haloalkyl, A preferably represents hydrogen or in each case optionally halogen-substituted $C_1$-$C_6$-alkyl or $C_3$-$C_8$-cycloalkyl, B preferably represents hydrogen, methyl or ethyl, A, B and the carbon atom to which they are attached preferably represent saturated $C_3$-$C_6$-cycloalkyl in which optionally one ring member has been replaced by oxygen or sulphur and which is optionally substituted once or twice by $C_1$-$C_4$-alkyl, trifluoromethyl or $C_1$-$C_4$-alkoxy, D preferably represents NH or oxygen, G preferably represents hydrogen (a) or represents one of the groups

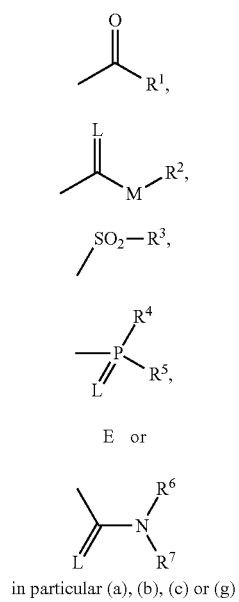

in particular (a), (b), (c) or (g)

in which
E represents a metal ion or an ammonium ion,
L represents oxygen or sulphur and
M represents oxygen or sulphur, $R^1$ preferably represents in each case optionally halogen-substituted $C_1$-$C_{10}$-alkyl, $C_2$-$C_{10}$-alkenyl, $C_1$-$C_4$-alkoxy-$C_1$-$C_4$-alkyl, $C_1$-$C_4$-alkylthio-$C_1$-$C_4$-alkyl or optionally fluorine-, chlorine-, $C_1$-$C_4$-alkyl- or $C_1$-$C_2$-alkoxy-substituted $C_3$-$C_6$-cycloalkyl, represents optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl, represents in each case optionally chlorine- or methyl-substituted pyridyl or thienyl, $R^2$ preferably represents in each case optionally fluorine- or chlorine-substituted $C_1$-$C_{10}$-alkyl, $C_2$-$C_{10}$-alkenyl, $C_1$-$C_4$-alkoxy-$C_2$-$C_4$-alkyl, represents optionally methyl- or methoxy-substituted $C_5$-$C_6$-cycloalkyl or represents in each case optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl or benzyl, $R^3$ preferably represents optionally fluorine-substituted $C_1$-$C_4$-alkyl or represents optionally fluorine-, chlorine-, bromine-, $C_1$-$C_4$-alkyl-, $C_1$-$C_4$-alkoxy-, trifluoromethyl-, trifluoromethoxy-, cyano- or nitro-substituted phenyl, $R^4$ preferably represents in each case optionally fluorine- or chlorine-substituted $C_1$-$C_4$-alkyl, $C_1$-$C_4$-alkoxy, $C_1$-$C_4$-alkylamino, $C_1$-$C_4$-alkylthio or represents in each case optionally fluorine-, chlorine-, bromine-, nitro-, cyano-, $C_1$-$C_4$-alkoxy-, trifluoromethoxy-, $C_1$-$C_4$-alkylthio-, $C_1$-$C_4$-haloalkylthio-, $C_1$-$C_4$-alkyl- or trifluoromethyl-substituted phenyl, phenoxy or phenylthio, $R^5$ preferably represents $C_1$-$C_4$-alkoxy or $C_1$-$C_4$-thioalkyl, $R^6$ preferably represents $C_1$-$C_6$-alkyl, $C_3$-$C_6$-cycloalkyl, $C_1$-$C_6$-alkoxy, $C_3$-$C_6$-alkenyl or $C_1$-$C_4$-alkoxy-$C_1$-$C_4$-alkyl, $R^7$ preferably represents $C_1$-$C_6$-alkyl, $C_3$-$C_6$-alkenyl or $C_1$-$C_4$-alkoxy-$C_1$-$C_4$-alkyl, $R^6$ and $R^7$ together preferably represent an optionally methyl- or ethyl-substituted $C_3$-$C_6$-alkylene radical in which optionally one carbon atom has been replaced by oxygen or sulphur in the form of their isomer mixtures or pure isomers.

Particular preference is given to using active compound combinations comprising compounds of formula (I) mentioned above in which the radicals have the following meaning:

W particularly preferably represents hydrogen, methyl, ethyl, chlorine, bromine or methoxy, X particularly preferably represents chlorine, bromine, methyl, ethyl, propyl, isopropyl, methoxy, ethoxy or trifluoromethyl, Y and Z particularly preferably independently of one another represent hydrogen, fluorine, chlorine, bromine, methyl, ethyl, propyl, isopropyl, trifluoromethyl or methoxy, A particularly preferably represents methyl, ethyl, propyl, isopropyl, butyl, isobutyl, sec-butyl, tert-butyl, cyclopropyl, cyclopentyl or cyclohexyl, B particularly preferably represents hydrogen, methyl or ethyl,
or A, B and the carbon atom to which they are attached particularly preferably represent saturated $C_5$-$C_6$-cycloalkyl in which optionally one ring member has been replaced by oxygen and which is optionally monosubstituted by methyl, ethyl, trifluoromethyl, methoxy, ethoxy, propoxy or butoxy, D particularly preferably represents NH or oxygen, G particularly preferably represents hydrogen (a) or represents one of the groups

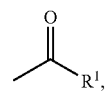

-continued

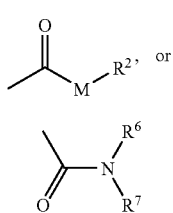

in which

M represents oxygen or sulphur,

R¹ particularly preferably represents $C_1$-$C_8$-alkyl, $C_2$-$C_4$-alkenyl, methoxymethyl, ethoxy-methyl, ethylthiomethyl, cyclopropyl, cyclopentyl or cyclohexyl, represents phenyl which is optionally mono- or disubstituted by fluorine, chlorine, bromine, cyano, nitro, methyl, ethyl, methoxy, trifluoromethyl or trifluoromethoxy, represents in each case optionally chlorine- or methyl-substituted pyridyl or thienyl, R² particularly preferably represents $C_1$-$C_8$-alkyl, $C_2$-$C_4$-alkenyl, methoxyethyl, ethoxyethyl or represents phenyl or benzyl, R⁶ and R⁷ independently of one another particularly preferably represent methyl, ethyl or together represent a $C_5$-alkylene radical in which the $C_3$-methylene group has been replaced by oxygen in the form of their isomer mixtures or pure isomers.

Very particular preference is given to using active compound combinations comprising compounds of the formula (I) mentioned above in which the radicals have the following meaning:

W very particularly preferably represents hydrogen or methyl,

X very particularly preferably represents chlorine, bromine or methyl,

Y and Z very particularly preferably independently of one another represent hydrogen, chlorine, bromine or methyl, A, B and the carbon atom to which they are attached very particularly preferably represent saturated $C_5$-$C_6$-cycloalkyl in which optionally one ring member has been replaced by oxygen and which is optionally monosubstituted by methyl, trifluoromethyl, methoxy, ethoxy, propoxy or butoxy, D very particularly preferably represents NH or oxygen, G very particularly preferably represents hydrogen (a) or represents one of the groups

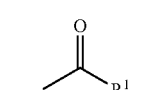

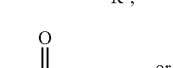

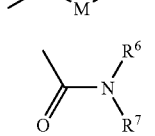

in which

M represents oxygen or sulphur,

R¹ very particularly preferably represents $C_1$-$C_8$-alkyl, $C_2$-$C_4$-alkenyl, methoxymethyl, ethoxy-methyl, ethylthiomethyl, cyclopropyl, cyclopentyl, cyclohexyl or represents phenyl which is optionally monosubstituted by fluorine, chlorine, bromine, methyl, methoxy, trifluoromethyl, trifluoromethoxy, cyano or nitro, represents in each case optionally chlorine- or methyl-substituted pyridyl or thienyl, R² very particularly preferably represents $C_1$-$C_8$-alkyl, $C_2$-$C_4$-alkenyl, methoxyethyl, ethoxy-ethyl, phenyl or benzyl, R⁶ and R⁷ independently of one another very particularly preferably represent methyl, ethyl or together represent a $C_5$-alkylene radical in which the $C_3$-methylene group has been replaced by oxygen in the form of their isomer mixtures or pure isomers.

With a special preference it is possible to employ active compound combinations comprising compounds of the formula (I) from the following patents/patent applications, cited on page 1, in which the radicals A, B, D, G, W, X, Y, Z, R¹, R², R⁶ and R⁷ have the definitions stated in the very particularly preferred ranges: EP-A-528 156, WO 97/01535, WO 97/36868, WO 98/05638, WO 04/007448.

Highlighted from these applications, the following compounds of the formula (I)

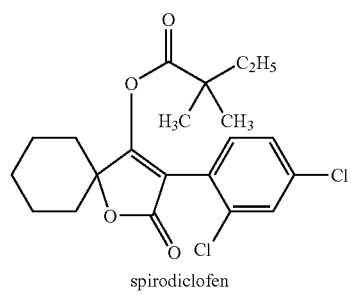

spirodiclofen

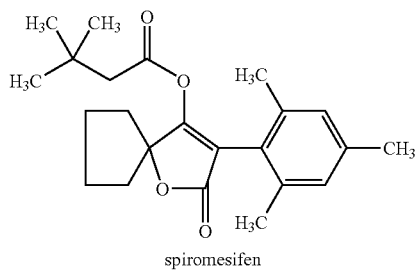

spiromesifen

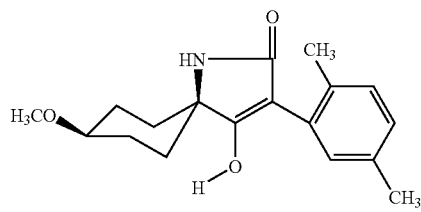

-continued

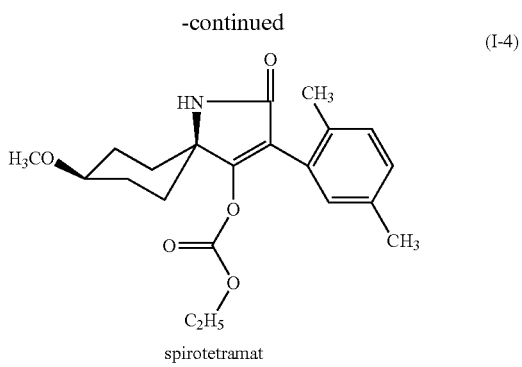

spirotetramat (I-4)

can be employed for active compound combinations with spinetoram.

The insecticidal and/or acaricidal action of the active compound combinations of the invention is, surprisingly, substantially higher than the sum of the actions of the individual active compounds. The unforeseeable effect is a true synergistic effect and not merely a complementarity of action.

As well as at least one active compound of the formula (I), the active compound combinations of the invention comprise spinetoram.

When the active compounds are present in the active compound combinations of the invention in certain proportions by weight, the synergistic effect is particularly marked. However, the weight ratios of the active compounds in the active compound combinations can be varied within a relatively broad range. Generally speaking, the combinations according to the invention comprise active compounds of the formula (I) and the co-components in the preferred, particularly preferred and very particularly preferred proportions indicated in the tables which now follow:

The mixing ratios are based on weight ratios. The ratio is to be understood as meaning active compound of the formula (I):spinetoram

| Co-component | Preferred mixing ratio | Particularly preferred mixing ratio | Very particularly preferred mixing ratio |
|---|---|---|---|
| spirodiclofen (I-1) | 25:1 to 1:25 | 10:1 to 1:10 | 5:1 to 1:5 |
| spiromesifen (I-2) | 25:1 to 1:25 | 10:1 to 1:10 | 5:1 to 1:5 |
| (I-3) | 25:1 to 1:25 | 10:1 to 1:10 | 5:1 to 1:5 |
| spirotetramat (I-4) | 25:1 to 1:25 | 10:1 to 1:10 | 5:1 to 1:5 |

In addition, the active compound combinations may also comprise further fungicidally, acaricidally or insecticidally active admix components.

In the context of the present invention, the term "active compound combination" denotes various combinations of active compounds of the formula (I) and spinetoram, for example in the form of a single ready-mix, in a combined spray mixture consisting of separate formulations of the individual active compounds, for example a tank mix, or in a combined use of the individual active compounds when these are applied sequentially, for example one after the other within a suitably short period, for example a few hours or days. In accordance with a preferred embodiment, the sequence of the application of the active compounds of the formula (I) and spinetoram is not critical for carrying out the present invention.

The active compound combinations according to the invention are well tolerated by plants, have favourable toxicity to warm-blooded species, show good environmental compatibility and are suitable for protecting plants and plant organs, for increasing harvest yields, for improving the quality of the harvest crop and for controlling animal pests, in particular insects, arachnids, helminths, nematodes and molluscs, which are found in agriculture, in horticulture, in animal breeding, in forests, in gardens and leisure facilities, in the protection of stored products and materials, and in the hygiene sector. They are preferably employed as plant protection agents. They are active against normally sensitive and resistant species and against all or individual developmental stages. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnostema consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp.,

*Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropod, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoans, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Athalia* spp., *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Acromyrmex* spp., *Atta* spp., *Cornitermes cumulans*, *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina*.

The plant-parasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

The active compound can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

According to the invention, a carrier is a natural or synthetic, organic or inorganic solid or liquid substance with which the active compounds are mixed or bonded for better applicability, in particular for application to plants or parts of plants. The carrier, which may be solid or liquid, is generally inert and should be suitable for use in agriculture.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as paper, sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol/POE and/or POP ethers, acid and/or POP/POE esters, alkylaryl and/or POP/POE ethers, fat and/or POP/POE adducts, POE and/or POP polyol derivatives, POE and/or POP/sorbitan or sugar adducts, alkyl or aryl sulphates, sulphonates and phosphates, or the corresponding PO ether adducts. Furthermore suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are fragrances, mineral or vegetable, optionally modified, oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve the chemical and/or physical stability may also be present.

The formulations generally comprise from 0.1 to 95% by weight of active compound, preferably from 0.5 to 90%.

The active compound combinations according to the invention can be present in commercially available formulations and in the use forms prepared from these formulations as a mixture with other active compounds such as insecticides, attractants, sterilants, bactericides, acaricides, nematicides, fungicides, growth regulators, herbicides, safeners, fertilizers or semiochemicals.

When used as insecticides, the active compound combinations according to the invention, in their commercially available formulations and in the use forms prepared from these formulations, may furthermore be present as a mixture with synergists. Synergists are compounds by which the activity of the active compounds is increased without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

Application is carried out in a conventional manner adapted to the use forms.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compound combination is carried out directly or by action on their environment, habitat or storage area according to customary treatment methods, for example by dipping, spraying, evaporating, atomizing, broadcasting, brushing-on, injection and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated.

The treatment method according to the invention is preferably applied to genetically modified organisms, such as, for example, plants or plant parts.

Genetically modified plants (or transgenic plants) are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which is/are present in the plant (using, for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, larger fruits, greater plant height, greener leaf colour, earlier flowering, better quality and/or a higher nutritional value of the harvested products, higher sugar concentration in the fruits, better storage stability and/or processability of the harvested products are possible which exceed the effects which were actually to be expected.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) compounds are to be understood as meaning, in the present context, those compounds or combinations of compounds which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compound combinations.

Plants which are also preferably to be treated according to the invention are resistant against one or more biotic stresses, i.e. said plants show a better defence against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stress factors.

Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis or the hybrid effect which results in generally higher yield, vigour, health and resistance towards biotic and abiotic stress factors. Such plants are typically made by crossing an inbred male sterile parent line (the female parent) with another inbred male fertile parent line (the male parent).

Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy4 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MLR 604;

5) an insecticidal secreted protein from *Bacillus thuringiensis* or *Bacillus cereus*, or an insecticidal portion thereof, such as the vegetative insecticidal proteins (VIP) listed at: http:// www.lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants.

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as, for example:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.

2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) transgenic plants which produce hyaluronan.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes, b) plants, such as cotton plants, which contain an altered form of rsw2 or rsw3 homologous nucleic acids;

c) plants, such as cotton plants, with an increased expression of sucrose phosphate synthase;

d) plants, such as cotton plants, with an increased expression of sucrose synthase;

e) plants, such as cotton plants, wherein the timing of the plasmodesmatal gating at the basis of the fibre cell is altered, for example through downregulation of fibre-selective β-1,3-glucanase;

f) plants, such as cotton plants, which have fibres with altered reactivity, for example through the expression of the N-acetylglucosamine transferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Particularly useful transgenic plants which may be treated according to the invention are plants which comprise one or more genes which encode one or more toxins and are the following which are sold under the trade names YIELD GARD® (for example maize, cotton, soya beans), Knock-Out® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

According to the invention, the plants listed can be treated particularly advantageously with the active compound combination according to the invention. The preferred ranges indicated above for the mixtures also apply to the treatment of these plants. Particular emphasis is given to treating the plants with the active compound combination specifically indicated in the present text.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, according to S. R. Colby, Weeds 15 (1967), 20-22:

If

X is the kill rate, expressed as a percentage of the untreated control, when employing active compound A at an application rate of m g/ha or in a concentration of m ppm, Y is the kill rate, expressed as a percentage of the untreated control, when employing active compound B at an application rate of n g/ha or in a concentration of n ppm and E is the kill rate, expressed as a percentage of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the kill of the combination is superadditive, i.e. a synergistic effect is present. In this case, the actually observed kill rate must exceed the value calculated using the above formula for the expected kill rate (E).

EXAMPLE A

*Myzus persicae* test

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Cabbage leaves (*Brassica oleracea*) which are heavily infested by the green peach aphid (*Myzus persicae*) are treated by spraying with the active compound preparation of the desired concentration.

After the desired period of time, the kill in % is determined. 100% means that all aphids have been killed; 0% means that none of the aphids have been killed. The kill rates determined are entered into Colby's formula.

In this test, for example, the following active compound combination in accordance with the present application shows a synergistically enhanced activity compared to the active compounds applied individually:

TABLE A

| *Myzus persicae* test | | | |
|---|---|---|---|
| Active compound | Concentration in g/ha | Kill in % after $6^d$ | |
| | | found* | calc.** |
| spinetoram | 20 | 0 | |
| | 0.16 | 0 | |
| spiromesifen | 100 | 50 | |
| spinetoram + spiromesifen (1:5) according to the invention | 20 + 100 | 80 | 50 |
| spirotetramat | 0.8 | 0 | |
| spinetoram + spirotetramat (1:5) according to the invention | 0.16 + 0.8 | 60 | 0 |

*found = activity found
**calc. = activity calculated using the Colby formula

EXAMPLE B

*Phaedon cochleariae* larvae test

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Cabbage leaves (*Brassica oleracea*) are treated by spraying with the active compound preparation of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are entered into Colby's formula.

In this test the following active compound combinations in accordance with the present application show a synergistically enhanced activity compared to the active compounds applied individually:

TABLE B-1

| *Phaedon cochleariae* larvae test | | |
|---|---|---|
| Active compound | Concentration in g/ha | Kill in % after $2^d$ |
| spinetoram | 4 | 50 |
| spirotetramat | 20 | 0 |

TABLE B-1-continued

Phaedon cochleariae larvae test

|  | found* | calc.** |
|---|---|---|
| spinetoram + spirotetramat (1:5) according to the invention | 4 + 20 | 83 | 50 |

| Active compound | Concentration in g/ha | Kill in % after $6^d$ |
|---|---|---|
| spinetoram | 0.8 | 50 |
| spiromesifen | 4 | 0 |

|  | found* | calc.** |
|---|---|---|
| spinetoram + spiromesifen (1:5) according to the invention | 0.8 + 4 | 83 | 50 |

*found = activity found
**calc. = activity calculated using the Colby formula

EXAMPLE C

Spodoptera frugiperda larvae test

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Cabbage leaves (*Brassica oleracea*) are treated by spraying with the active compound preparation of the desired concentration and are populated with larvae of the army worm (*Spodoptera frugiperda*) while the leaves are still moist.

After the desired period of time, the kill in % is determined. 100% means that all caterpillars have been killed; 0% means that none of the caterpillars have been killed. The kill rates determined are entered into Colby's formula.

In this test the following active compound combinations in accordance with the present application show a synergistically enhanced activity compared to the active compounds applied individually:

TABLE C-1

Spodoptera frugiperda test

| Active compound | Concentration in g/ha | Kill in % after $6^d$ |
|---|---|---|
| spinetoram | 0.16 | 83 |
| spirodiclofen | 0.8 | 0 |

|  | found* | calc.** |
|---|---|---|
| spinetoram + spirodiclofen (1:5) according to the invention | 0.16 + 0.8 | 100 | 83 |
| spiromesifen | 0.8 | 0 |

|  | found* | calc.** |
|---|---|---|
| spinetoram + spiromesifen (1:5) according to the invention | 0.16 + 0.8 | 100 | 83 |
| spirotetramat | 0.8 | 0 |

TABLE C-1-continued

Spodoptera frugiperda test

| Active compound | Concentration in g/ha | Kill in % after $6^d$ |
|---|---|---|

|  | found* | calc.** |
|---|---|---|
| spinetoram + spirotetramat (1:5) according to the invention | 0.16 + 0.8 | 100 | 83 |

*found = activity found
**calc. = activity calculated using the Colby formula

EXAMPLE D

Tetranychus test (OP-resistant/spray treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of bean leaves (*Phaseolus vulgaris*) which are infested by all stages of the greenhouse red spider mite (*Tetranychus urticae*) are sprayed with an active compound preparation of the desired concentration.

After the desired period of time, the activity in % is determined. 100% means that all spider mites have been killed; 0% means that none of the spider mites have been killed.

In this test, the following active compound combination in accordance with the present application showed a synergistically enhanced activity compared to the active compounds applied individually:

TABLE D-1

Tetranychus urticae test

| Active compound | Concentration in g/ha | Kill in % after $2^d$ |
|---|---|---|
| spinetoram | 0.8 | 0 |
| spiromesifen | 4 | 0 |

|  | found* | calc.** |
|---|---|---|
| spinetoram + spiromesifen (1:5) according to the invention | 0.8 + 4 | 20 | 0 |

*found = activity found
**calc. = activity calculated using the Colby formula

The invention claimed is:

1. An active compound composition comprising a compound of the formula (I) which is a compound of formula (I-1):

a compound of the formula (I-2)

a compound of the formula (I-3)

or
a compound of the formula (I-4)

in the form of isomer mixtures or pure isomers
and spinetoram.

2. The active compound composition according to claim 1 further comprising an extender, a surfactant, or a combination thereof.

3. The active compound composition according to claim 1, wherein the weight ratio of the compound of the formula (I) to spinetoram is from 25:1 to 1:25.

4. The active compound composition according to claim 3, wherein the weight ratio is from 10:1 to 1:10.

5. The active compound composition according to claim 4, wherein the weight ratio is from 5:1 to 1:5.

6. The active compound composition according to claim 1, wherein the compound of formula (I) is (I-4), wherein the weight ratio of the compound of the formula (I-4) to spinetoram is from 25:1 to 1:25.

7. The active compound composition according to claim 6, wherein the weight ratio is from 10:1 to 1:10.

8. The active compound composition according to claim 7, wherein the weight ratio is from 5:1 to 1:5.

9. A method of controlling insects or acarids, comprising contacting plants or their environment with the active compound composition according to claim 1.

10. The method according to claim 9, wherein the compound of the formula (I) is (I-4), and wherein the weight ratio of (I-4) to spinetoram is from 25:1 to 1:25.

11. A process for preparing an insecticidal and/or an acaricidal composition, comprising mixing the active compound composition according to claim 1 with an extender, a surfactant, or a combination thereof.

12. The process according to claim 11, wherein the compound of the formula (I) is (I-4), and wherein the weight ratio of (I-4) to spinetoram is from 25:1 to 1:25.

13. A method of controlling insects or acarids, comprising contacting said insects or acarids and/or their habitat with a compound of the formula (I) which is a compound of formula (I-1):

a compound of the formula (I-2)

a compound of the formula (I-3)

or
a compound of the formula (I-4)
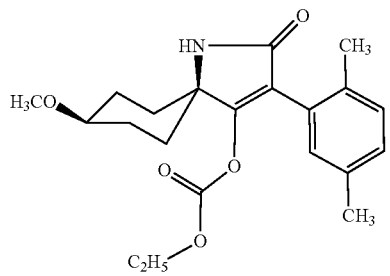
in the form of isomer mixtures or pure isomers
and spinetoram; and
wherein the compound of the formula (I) and spinetoram may be applied separately or together in the same composition.
14. The method according to claim 13, wherein the compound of the formula (I) is (I-4), and wherein the weight ratio of (I-4) to spinetoram is from 25:1 to 1:25.
* * * * *